United States Patent [19]
Bailey

[11] 3,963,746
[45] June 15, 1976

[54] 4,5 DIHALOPYRROL 2-YL DI AND TRI HALOMETHYL KETONES

[75] Inventor: Denis M. Bailey, East Greenbush, N.Y.

[73] Assignee: Sterling Drug Inc., New York, N.Y.

[22] Filed: Apr. 28, 1975

[21] Appl. No.: 572,430

Related U.S. Application Data

[63] Continuation-in-part of Ser. No. 350,086, March 11, 1973, Pat. No. 3,918,954.

[52] U.S. Cl............................ 260/326.5 J; 424/274
[51] Int. Cl.$^2$...................................... C07D 207/36
[58] Field of Search ............................ 260/326.5 J

[56] References Cited
UNITED STATES PATENTS
3,560,523   2/1971   Etienne et al................. 260/326.5 J

OTHER PUBLICATIONS

Perry et al. "J. Inorg. Nucl. Chem." (1971) pp. 1031–1039, vol. 33.
Sanna et al., "Gazz. Chim. Ital." 63, 479–484 (1933).

*Primary Examiner*—Raymond V. Rush
*Assistant Examiner*—David E. Wheeler
*Attorney, Agent, or Firm*—William G. Webb; B. W. Wyatt

[57] ABSTRACT

4,5-Dihalopyrrol-2-yl di- and trihalomethyl ketones, prepared by reaction of pyrrole with a di- or trihaloacetyl halide or with a di- or trihaloacetic anhydride and halogenation of the resulting pyrrol-2-yl di- or trihalomethyl ketone, useful as antibacterial, herbicidal and insecticidal agents.

18 Claims, No Drawings

4,5 DIHALOPYRROL 2-YL DI AND TRI HALOMETHYL KETONES

RELATED APPLICATIONS

This is a continuation-in-part of my prior, copending application Ser. No. 350,086, filed Mar. 11, 1973 now U.S. Pat. No. 3,918,954, 11-11-75.

BACKGROUND OF THE INVENTION a. Field of the Invention

This invention relates to 4,5-dihalopyrrol-2-yl di- and trihalomethyl ketones useful as antibacterial, post-emergence herbicidal and insecticidal agents.

b. Description of the Prior Art

Pyrrol-2-yl di- and trichloromethyl ketones are known [Sanna et al., Gazz, chim, ital. 63, 479–84 (1933); Chem. Abs. 28, 763 (1934)]. These known compounds have not previously been known to have any utility other than as laboratory curiosities. It has been found that when these known compounds are halogenated in the 4- and 5-positions of the pyrrole ring with chlorine, bromine or iodine, compounds are produced having general antibacterial activity superior to that of the known prior art species.

SUMMARY OF THE INVENTION

This invention relates in a composition of matter aspect to 4,5-di-X-1R-pyrrol-2-yl di- and trihalomethyl ketones, where X is chlorine, bromine or iodine and R is hydrogen or lower-alkyl, which are useful as antibacterial, post-emergence herbicidal and insecticidal agents.

DETAILED DESCRIPTION INCLUSIVE OF THE PREFERRED EMBODIMENTS

More specifically, this invention relates to 4,5-dihalopyrrol-2-yl di- and trihalomethyl ketones having the formula:

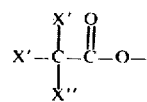

I wherein X is chlorine, bromine or iodine, both values of X being identical; X' is chlorine or fluorine, both values of X' being identical; X" is either hydrogen or chlorine or fluorine identical with X'; and R is hydrogen or lower-alkyl.

Preferred compounds of the invention within the ambit of formula I are those where R is hydrogen.

As used herein, the term "lower-alkyl" means saturated, monovalent, aliphatic radicals, including straight or branched-chain radicals, of from one to four carbon atoms, as illustrated by methyl, ethyl, propyl, isopropyl, butyl, sec.-butyl and isobutyl.

The compounds of formula I are prepared by reaction of pyrrole with a di- or trihaloacetyl halide or with a di- or trihaloacetic anhydride, followed by halogenation of the resulting pyrrol-2-yl di- or trihalomethyl ketone and, if appropriate, N-alkylation of the resulting 4,5-dihalopyrrol-2-yl di- or trihalomethyl ketone. The method is represented by the following reaction sequence:

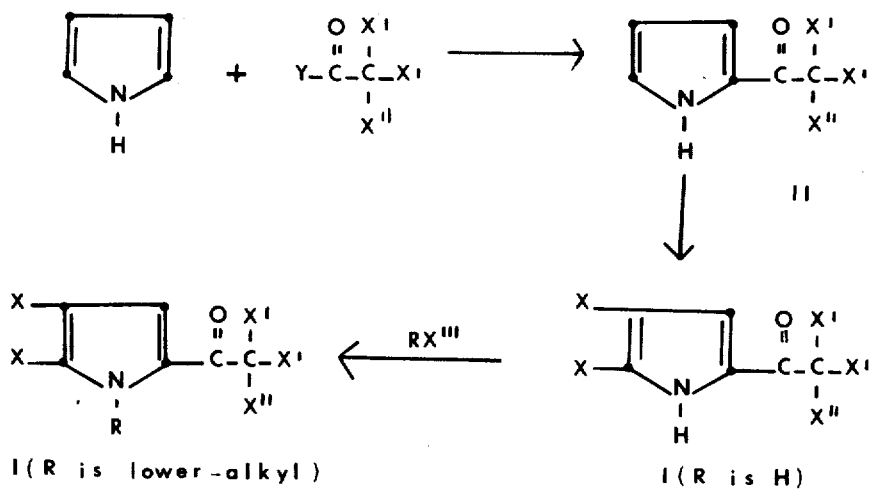

wherein X, X', X", and R have the meanings given above, X''' represents halogen, and Y represents either a halogen atom or the group $$X'-\underset{X''}{\overset{X'}{\underset{|}{C}}}-\overset{O}{\underset{}{\overset{\|}{C}}}-O-$$

where X' and X" have the meanings given above. The reaction of pyrrole with the di- or trihaloacetyl halide or the di- or trihaloacetic anhydride takes place readily at room temperature by direct interaction of the two reactants in an aprotic organic solvent, for example diethyl ether, dioxane, or tetrahydrofuran.

Conversion of the pyrrol-2-yl di- or trihalomethyl ketones of formula II to the 4,5-dihalopyrrol-2-yl di- or trihalomethyl ketones of formula I where R is hydrogen is carried out by direct halogenation of the former with elemental chlorine or bromine (to prepare the compounds where X is chlorine or bromine, respectively), or with iodine monochloride (to prepare the compounds of formula I where X is iodine). The halogenation reaction is carried out at a temperature in the range from about 0°C. to about 20°C., and in an organic solvent inert under the conditions of the reaction, for example glacial acetic acid, chloroform, carbon tetrachloride, methylene dichloride, ethylene dichloride, and the like.

Alkylation of the products thus formed to the compounds of formula I where R is lower-alkyl is effected by reaction of the compounds of formula I where R is hydrogen with a lower-alkyl halide in an inert organic solvent, for example dimethylformamide or acetone, and in the presence of an acid-acceptor, for example sodium or potassium carbonate. The reaction is advantageously carried out at the reflux temperature of the reaction mixture.

The compounds of formula I have been found to possess antibacterial activity. The antibacterial activity was determined using a modification of the Autotiter method described by Goss et al., Applied Microbiology, 16 (No. 9), 1414–1416 (1968) in which a 1000 mcg./ml. solution of the test compound is prepared. To the first cup of the Autotray is added 0.1 ml. of the test solution. Activation of the Autotiter initiates a sequence of operations by which 0.05 ml. of the test compound solution is withdrawn from this cup by a Microtiter transfer loop and diluted in 0.05 ml. of sterile semisynthetic medium (glucose). After this operation, 0.05 ml. of inoculated semi-synthetic medium is added automatically to each cup. The overall operation results in final drug concentrations ranging from 500 to 0.06 mcg./ml. in twofold decrements. The Autotray is incubated for 18–20 hours at 37°C., at which time the trays are examined visually for growth as evidenced by turbidity, and the concentration of the last sample in the series showing no growth (or no turbidity) is recorded as the minimal inhibitory concentration (MIC). The compounds of formula I were thus found to be antibacterially effective against *Staphylococcus aureus*, *Pseudomonas aeruginosa*, *Escherichia coli*, and *Proteus vulgaris* at concentrations from 2 to 500 mcg./ml.

In standard biological test procedures, certain compounds within the ambit of formula I have also been found to possess herbicidal and insecticidal activities. Specifically, the following compounds of formula I have been found to possess post-emergence herbicidal activity:

| X | X' | X'' | R |
|---|----|-----|---|
| Br | Cl | Cl | H |
| Cl | Cl | Cl | H |
| Br | Cl | H | H |
| Cl | F | F | H |
| I | Cl | Cl | H |

The first two above-listed species, where X is either Br or Cl and X' and X'' in both cases is Cl, while R in both bases is H, have been found to have insecticidal activity against spider mites, the Lethal Concentration$_{50}$ being, respectively, 210 p.p.m. and 80 p.p.m.

Post-emergence herbicidal activity was determined as follows: Test crop seeds of lima beans, corn, lettuce, mustard and crabgrass were planted in shallow flat-bed trays containing two to three inches of a loam soil, and the growth trays were maintained in a greenhouse and regularly watered for approximately 2 weeks. When the first trifoliate leaves of bean plants were unfolding, the test plants were removed from the greenhouse and sprayed with an aqueous-acetone solution of the compound being tested at a rate equivalent to 8 pounds of the active ingredient per acre. The plants were maintained in the greenhouse and watered regularly for an additional 2 weeks after which time the individual plant species were examined for percent kill. In addition, surviving plants were scored for overall vigor according to the following scale:

5- No effect on plants
4- Slight injury to surviving plants
3- Moderate injury to surviving plants
2- Severe injury to surviving plants
1- Surviving plants are so badly injured they will die.

Plants receiving no chemical treatment were maintained for comparison.

Insecticidal activity was evaluated against adult mites in the following way: Leaves of pinto beans (*Phaseolus vulgaris*) were infested with two-spotted spider mites (*Tetranychus urticae*) by placing a small section of highly infested plant leaf, containing 50 to 75 adult female mites, in an inverted position on the upper leaf surface of a growing bean seedling. After 2 to 4 hours, when mite migration to the growing plant leaf was complete, the seedling leaves were briefly immersed in 10% acetone in water solution containing the test compound at the desired concentration. Plants were maintained at 80°F. and 50% relative humidity for 48 hours, after which time counts were taken of dead and living female mites.

The actual determination of the numerical biological data definitive for a particular compound of formula I is readily determined by standard test procedures by technicians versed in biological test procedures, without the need for any extensive experimentation.

When used as antibacterial agents, the compounds of formula I can be formulated for use by preparing a dilute solution in an organic medium in which the compounds are soluble, for example ethyl alcohol or in such solution containing a surfactant, and are applied to a surface to be disinfected by conventional methods such as spraying, swabbing, immersion, and the like. Alternatively, the compounds can be formulated as ointments or creams by incorporating them in conventional ointment or cream bases, for example alkylpolyether alcohols, cetyl alcohol, stearyl alcohol, and the like, or as jellies by incorporating them in conventional jelly bases such as glycerol and tragacanth. They can also be formulated for use as aerosol sprays or foams.

For herbicidal applications, the 4,5-dihalopyrrol-2-yl di- and trihalomethyl ketones of the invention may be utilized in diverse formulations, including agricultural adjuvants and agricultural carriers, i.e. those materials normally employed to facilitate the dispersion of active ingredients in agricultural applications, recognizing the fact that the formulation and mode of application of a toxicant may affect the activity of the material in a given application. Thus, the compounds of this invention may be formulated as granules of relatively large particle size, as wettable powders, as emulsifiable concentrates, as solutions, or as any of several other known types of formulations, depending on the desired mode of application.

Granular formulations are particularly useful for aerial distribution or for penetration of a canopy of foliage. Useful granular formulations may be of several types. Impregnated granules are those wherein the active ingredient is applied to large particles of an absorbent carrier, such as an attapulgite or kaolin clay, corncobs, expanded mica, etc., normally in the form of a solution in a solvent. Surface-coated granules may be produced by spraying the molten active ingredient onto the surface of a generally nonabsorbent particle or by spraying on a solution of active ingredient in a solvent. The core may be water-soluble such as a prilled fertilizer, or insoluble such as sand, marble chips or coarse talc. Particularly useful is a granule wherein a wettable powder is applied as a surface coating to a sand or other insoluble particle such that the wettable may be dispersed on contact of the granule with moisture. Granules may be produced by agglomeration of dusts or powders by compaction rollers, by extrusion through a die or by use of a granulating disc. Granular formulations may vary widely in concentration, with useful formulations containing as little as 0.5% or as much as 95% of active ingredient.

Wettable powders, also useful formulations for both pre- and post-emergence herbicides, are in the form of finely divided particles which disperse readily in water or other dispersants. The wettable powder is ultimately applied to the soil either as a dry dust or as an emulsion in water or other liquid. Typical carriers for wettable powders include fuller's earth, kaolin clays, silicas and other highly absorbent, readily wet inorganic diluents. Wettable powders normally are prepared to contain about 5% to 80% of active ingredient, depending on the absorbency of the carrier, and usually also contain a small amount of a wetting, dispersing or emulsifying agent to facilitate dispersion. For example, a useful wettable powder formulation contains 80.8 parts of a 4,5-dihalopyrrol-2-yl di- or trihalomethyl ketone of the invention, 17.9 parts of palmetto clay, and 1.0 part of sodium lignosulfonate and 0.3 part of a sulfonated aliphatic polyester as wetting agents.

Other useful formulations for herbicidal applications are emulsifiable concentrates, which are homogeneous liquid or paste compositions dispersible in water or other dispersant, and may consist entirely of a compound of the invention with a liquid or solid emulsifying agent, or may also contain an agriculturally acceptable liquid carrier, such as xylene, heavy aromatic naphthas, isophorone and other nonvolatile organic solvents.

Typical wetting, dispersing or emulsifying agents used in agricultural formulations include, for example, the alkyl and alkylaryl sulfonates and sulfates and their sodium salts; polyethylene oxides; sulfonated oils, fatty acid esters of polyhydric alcohols; and other types of surface-active agents, many of which are available in commerce. The surface-active agent, when used, normally comprises from 1% to 15% by weight of the herbicidal composition.

These formulations may be applied without further dilution or as dilute solutions, emulsions or suspensions in water or other suitable diluent. The compositions may be applied to the area wherein control is desired by spraying onto the undesired vegetation or onto the surface of the soil in the case of liquid compositions or by distribution from mechanical equipment in the case of solids. The surface-applied material may also be blended into the upper layer of soil by cultivation, or left as applied, as is appropriate to gain the optimum results with the particular treatment.

The active herbicidal compounds of this invention may be formulated and/or applied with insecticides, fungicides, nematicides, plant-growth regulators, fertilizers, and other agricultural chemicals. In applying the active compounds of the invention, whether formulated alone or with other agricultural chemicals, an effective amount and concentration of a 4,5-dihalopyrrol-2-yl di- or trihalomethyl ketone of the invention are of course employed.

The molecular structures of the compounds of the invention were assigned on the basis of study of their infrared, ultraviolet, and NMR spectra, and confirmed by the correspondence between calculated and found values for elementary analyses for the elements.

The following examples will further illustrate the invention without, however, limiting it thereto. All melting points are uncorrected.

EXAMPLE 1

A solution of 6.7 g. (0.1 mole) of pyrrole in 70 ml. of diethyl ether was added slowly and with vigorous stirring to a solution of 20 g. (0.11 mole) of trichloroacetyl chloride in 20 ml. of diethyl ether. When addition was complete, stirring was continued for another half hour, and the solution then treated cautiously with an excess of 10% aqueous potassium carbonate. When frothing had subsided, the organic layer was separated, dried, taken to dryness in vacuo, and the residual solid recrystallized with charcoaling from hexane to give 10.2 g. of pyrrol-2-yl trichloromethyl ketone, m.p. 74°–75°C.

The latter (0.05 mole) was dissolved in 25 ml. of glacial acetic acid, and the solution was treated slowly and with vigorous stirring with a solution of 16 g. (0.1 mole) of bromine in 25 ml. of glacial acetic acid. When addition was complete, the reaction mixture was warmed at about 50°C. on a water bath for about 15 minutes until the orange bromine color had disappeared. The solution was then concentrated to a small volume, treated cautiously with 10% aqueous potassium carbonate, and the mixture extracted with diethyl ether. The combined ether extracts, on drying and concentration, afforded a solid residue which was recrystallized from hexane to give 15.5 g. of 4,5-dibromopyrrol-2-yl trichloromethyl ketone, m.p. 136°–138°C.

EXAMPLE 2

Chlorine was bubbled into 450 ml. of glacial acetic acid until a total of 15.6 g. (0.22 mole) had been taken up. This solution was then added slowly and with vigorous stirring to a solution of 22.3 g. (0.11 mole) of pyrrol-2-yl trichloromethyl ketone (described above in Example 1) in 50 ml. of glacial acetic acid. The mixture was stirred for 2 hours, worked up using the procedure described above in Example 1, and the crude product thus obtained recrystallized from hexane to give 20.2 g. of 4,5-dichloropyrrol-2-yl trichloromethyl ketone, m.p. 129°–131°C.

EXAMPLE 3

A solution of 6.7 g. (0.10 mole) of pyrrole in 70 ml. of diethyl ether was added slowly and with vigorous stirring to a solution of 23 g. (0.11 mole) of trichloroacetic anhydride in 20 ml. of diethyl ether. The mixture was stirred for one hour, decomposed by the addition of 110 ml. of 10% aqueous potassium carbonate, and worked up using the procedure described above in Example 1. The crude product thus obtained was recrystallized from hexane to give 9.9 g. of pyrrol-2-yl trifluoromethyl ketone, m.p. 46°–47°C.

A solution of the latter (10.0 g., 0.062 mole) in 25 ml. of glacial acetic acid was treated dropwise with a solution of 19.8 g. (0.12 mole) of bromine in 25 ml. of glacial acetic acid. The mixture was worked up using the procedure described above in Example 1, and the product recrystallized from hexane to give three crops of product totaling 12.4 g. of 4,5-dibromopyrrol-2-yl trifluoromethyl ketone, m.p. 108°–109°C.

EXAMPLE 4

A solution of 67 g. (1.0 mole) of pyrrole in 700 ml. of diethyl ether was added slowly and with stirring to a solution of 160 g. (1.1 moles) of dichloroacetyl chloride in 200 ml. of diethyl ether. The resulting purple solution was decomposed by the addition of aqueous potassium carbonate, and the reaction mixture worked up using the procedure described above in Example 1. The product was recrystallized from hot hexane to give 75 g. of pyrrol-2-yl dichloromethyl ketone, m.p. 87°–89°C.

The latter (13 g., 0.073 mole), dissolved in 25 ml. of glacial acetic acid, was treated with a solution of 23.5 g. (0.15 mole) of bromine in 25 ml. of glacial acetic acid using the procedure described above in Example 1. The product was recrystallized from a diethyl ether/hexane mixture to give 19.4 g. of 4,5-dibromopyrrol-2-yl dichloromethyl ketone, m.p. 127°–129°C.

EXAMPLE 5

To a solution of 20 g. (0.11 mole) of pyrrol-2-yl dichloromethyl ketone (described above in Example 4) in 50 ml. of glacial acetic acid was added with stirring a solution of 16.6 g. (0.24 mole) of chlorine in glacial acetic acid. The reaction mixture was worked up using the procedure described above in Example 1, and the product recrystallized from a diethyl ether/hexane mixture to give 12.0 g. of 4,5-dichloropyrrol-2-yl dichloromethyl ketone, m.p. 104°–107°C.

EXAMPLE 6

A solution of 20 g. (0.12 mole) of pyrrol-2-yl trifluoromethyl ketone (described above in Example 3) in 50 ml. of glacial acetic acid was treated slowly and with vigorous stirring with a solution of 17.3 g. (0.24 mole) of chlorine in 450 ml. of glacial acetic acid. The reaction mixture was worked up using the procedure described above in Example 1 and the product recrystallized from a diethyl ether/hexane mixture to give 8.5 g. of 4,5-dichloropyrrol-2-yl trifluoromethyl ketone, m.p. 86°–87°C.

EXAMPLE 7

The mixture of 5.0 g. (0.015 mole) of 4,5-dibromopyrrol-2-yl dichloromethyl ketone (described above in Example 4), 6.6 g. (0.05 mole) of potassium carbonate and 3.2 g. (0.02 mole) of methyl iodide in 100 ml. of acetone was heated under reflux for about an hour and a half. The mixture was concentrated to a small volume and the residue partitioned between water and diethyl ether. The organic layer was separated, dried over sodium sulfate, concentrated to a small volume, and the residue placed on an alumina chromatographic column and eluted with a 1:4 mixture of ethyl acetate/hexane. The product segment of the column, which was located by ultraviolet illumination, was removed, extracted with methanol, and the methanol extract, after evaporation to dryness, recrystallized from diethyl ether/hexane to give 2.3 g. of 4,5-dibromo-1-methylpyrrol-2-yl dichloromethyl ketone, m.p. 127°–130°C.

By replacement of the methyl iodide used in the above described procedure with a molar equivalent amount of ethyl iodide, propyl iodide, isopropyl iodide, butyl iodide, sec.-butyl iodide or isobutyl iodide, there can be obtained, respectively, 4,5-dibromo-1-ethylpyrrol-2-yl dichloromethyl ketone;

4,5-dibromo-1-propylpyrrol-2-yl dichloromethyl ketone;

4,5-dibromo-1-isopropylpyrrol-2-yl dichloromethyl ketone;

4,5-dibromo-1-butylpyrrol-2-yl dichloromethyl ketone;

4,5-dibromo-1-sec.-butylpyrrol-2-yl dichloromethyl ketone; and 4,5-dibromo-1-isobutylpyrrol-2-yl dichloromethyl ketone.

EXAMPLE 8

A mixture of 5 g. (0.02 mole) of 4,5-dichloropyrrol-2-yl dichloromethyl ketone (described above in Example 5), 9.1 g. (0.07 mole) of potassium carbonate, and 4.3 g. (0.03 mole) of methyl iodide in 125 ml. of acetone was heated under reflux for an hour and a half, and the reaction mixture worked up using the procedure described above in Example 7. The crude product was recrystallized from a diethyl ether/hexane mixture to give 2.4 g. of 4,5-dichloro-1-methylpyrrol-2-yl dichloromethyl ketone, m.p. 114°–116°C.

EXAMPLE 9

A solution of 21.3 g. (0.10 mole) of pyrrol-2-yl trichloromethyl ketone (described above in Example 1) in 200 ml. of glacial acetic acid was heated on a steam bath and treated slowly and with stirring with 100 ml. of a 2.07N solution of sodium chloride/iodine monochloride in water. When addition was complete, the mixture was stirred and heated for an additional hour and a half, concentrated to a small volume and treated with an excess of a saturated aqueous sodium bicarbonate solution. The mixture was extracted with ether, the combined ether extracts dried, charcoaled and concentrated to dryness, and the residual solid recrystallized twice from a diethyl ether/hexane mixture to give 17.2 g. of 4,5-diiodopyrrol-2-yl trichloromethyl ketone, m.p. 176°–177°C.

EXAMPLE 10

A mixture of 15 g. (0.03 mole) of 4,5-diiodopyrrol-2-yl trichloromethyl ketone (described above in Example 9), 17 g. (0.12 mole) of anhydrous potassium carbonate, and 8.5 g. (0.06 mole) of methyl iodide in 150 ml. of acetone was heated under reflux for about thirty minutes, and the reaction mixture worked up using the procedure described above in Example 7. The crude product was recrystallized from hexane to give 10.3 g. of 4,5-diiodo-1-methylpyrrol-2-yl trichloromethyl ketone, m.p. 104°–105°C.

RESULTS OF BIOLOGICAL TESTING

Data, expressed in terms of the minimum inhibitory concentration in mcg./ml. obtained in in vitro tests of the compounds of the invention in comparison with the known compounds, pyrrol-2-yl dichloromethyl ketone (Reference Compound A) and pyrrol-2-yl trichloromethyl ketone (Reference Compound B), against the bacterial organisms *Staphylococcus aureus* 209, *Escherichia coli* 198, *Proteus vulgaris* 9920 and *Pseudomonas aeruginosa* 211 (identified as organisms A, B, C and D, respectively) are given in the table below.

| Example | A | B | C | D |
|---|---|---|---|---|
| Ref. A | 250 | 125 | 500 | 62.5 |
| Ref. B | 250 | 500 | 500 | 125 |
| 1 | 62.5 | >125 | 250 | 62.5 |
| 2 | 125 | 62.5 | 250 | 125 |
| 3 | 1.95 | 31.2 | 250 | 500 |
| 4 | 7.8 | 15.6 | 125 | 250 |
| 5 | 3.9 | 31.2 | 62.5 | 250 |
| 6 | 3.9 | 31.2 | 125 | >125 |
| 7 | 62.5 | >125 | >125 | 125 |
| 8 | 125 | >125 | >125 | >125 |
| 9 | 31.3 | 125 | >125 | >125 |

These results show that, as antibacterial agents against *Staphylococcus aureus* 209, *Escherichia coli* 198 and *Proteus vulgaris* 9920, the compounds of the invention are generally more active than either of the reference species, which have no ring halogen atom and which were not previously known to have any utility.

Data obtained in post-emergence herbicidal testing of the species of Examples 1, 2, 4, 6 and 9 at an application rate of 8 pounds of test compound per acre, expressed in terms of the percent kill of the plant species and the vigor rating of the surviving plants, are given below.

| Example | Lima Bean Vigor | Kill | Corn Vigor | Kill | Lettuce Vigor | Kill | Mustard Vigor | Kill | Crabgrass Vigor | Kill |
|---|---|---|---|---|---|---|---|---|---|---|
| 1 | 3 | 0 | 5 | 0 | 2 | 90 | 2 | 90 | 5 | 0 |
| 2 | 3 | 0 | 5 | 0 |  | 100 |  | 100 | 3 | 10 |
| 4 | 5 | 0 | 5 | 0 | 3 | 60 | 3 | 60 | 1 | 90 |
| 6 | 3 | 0 | 3 | 0 |  | 100 |  | 100 |  | 100 |
| 9 | 3 | 30 | 4 | 0 | 1 | 90 | 1 | 90 | 4 | 0 |

These results show that the compounds of the invention are uniformly herbicidally effective against lettuce and mustard, both broadleaf plants, thus indicating utility of the compounds as broadleaf herbicides. In addition, certain of the compounds, namely the species of Examples 4 and 6, have herbicidal activity against crabgrass thus indicating limited utility of the genus as herbicides against certain grasses.

I claim:
1. A compound having the formula

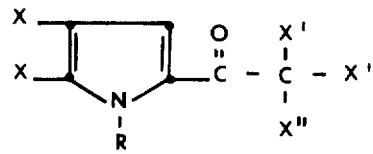

wherein each X is chlorine, bromine, or iodine, both values of X being identical; X' is chlorine or fluorine, both values of X' being identical; X" is either hydrogen or chlorine or fluorine identical with X'; and R is hydrogen or lower-alkyl.

2. A compound according to claim 1 wherein R is hydrogen.

3. A compound according to claim 1 wherein R is lower-alkyl.

4. A compound according to claim 2 wherein X' and X" are each chlorine.

5. A compound according to claim 2 wherein X' and X" are each fluorine.

6. A compound according to claim 2 wherein X' is chlorine and X" is hydrogen.

7. A compound according to claim 3 wherein X' and X" are each chlorine.

8. A compound according to claim 3 wherein X' is chlorine and X" is hydrogen.

9. 4,5-Dibromopyrrol-2-yl trichloromethyl ketone according to claim 4.

10. 4,5-Dichloropyrrol-2-yl trichloromethyl ketone according to claim 4.

11. 4,5-Diiodopyrrol-2-yl trichloromethyl ketone according to claim 4.

12. 4,5-Dibromopyrrol-2-yl trifluoromethyl ketone according to claim 5.

13. 4,5-Dichloropyrrol-2-yl trifluoromethyl ketone according to claim 5.

14. 4,5-Dibromopyrrol-2-yl dichloromethyl ketone according to claim 6.

15. 4,5-Dichloropyrrol-2-yl dichloromethyl ketone according to claim 6.

16. 4,5-Diiodo-1-methylpyrrol-2-yl trichloromethyl ketone according to claim 7.

17. 4,5-Dibromo-1-methylpyrrol-2-yl dichloromethyl ketone according to claim 8.

18. 4,5-Dichloro-1-methylpyrrol-2-yl dichloromethyl ketone according to claim 8.

* * * * *